United States Patent [19]

Jiles et al.

[11] Patent Number: 5,479,099
[45] Date of Patent: Dec. 26, 1995

[54] MAGNETIC INSPECTION HEAD SUITED FOR CONTOURED OR IRREGULAR SURFACES

[75] Inventors: David C. Jiles; David A. Kaminski, both of Ames, Iowa

[73] Assignee: Iowa State University Research Foundation, Inc., Ames, Iowa

[21] Appl. No.: 139,272

[22] Filed: Oct. 18, 1993

[51] Int. Cl.⁶ .......................... G01R 33/12; G01N 27/72; H01F 27/24
[52] U.S. Cl. .......................... 324/235; 324/239; 324/262; 324/222; 336/234
[58] Field of Search .................... 324/216–218, 324/222, 223, 228–230, 239–240, 235, 262, 220; 336/20, 234

[56] References Cited

U.S. PATENT DOCUMENTS

| | | | |
|---|---|---|---|
| 2,722,636 | 11/1955 | Minchom | 324/216 |
| 2,892,150 | 6/1959 | Nettles et al. | 324/220 |
| 3,064,127 | 11/1962 | Green et al. | 324/220 |
| 3,109,139 | 10/1963 | Branker | 324/240 |
| 3,311,818 | 3/1967 | Quittner | 324/209 |
| 3,427,872 | 2/1969 | Leep et al. | 73/88.5 |
| 3,593,122 | 3/1969 | Barton | 324/220 |
| 3,612,986 | 10/1971 | Rollwitz et al. | 324/209 |
| 3,742,357 | 6/1973 | Kubo et al. | 324/209 |
| 3,861,206 | 1/1975 | Kawafune et al. | 324/209 |
| 3,925,724 | 12/1975 | Steingroever | 324/243 |
| 3,976,935 | 8/1976 | Steingroever | 324/243 |
| 4,095,181 | 6/1978 | Harris et al. | 324/238 |
| 4,303,884 | 12/1981 | Malick | 324/220 |
| 4,316,146 | 2/1982 | Jilken | 324/209 |
| 4,379,261 | 4/1983 | Lakin | 324/240 |
| 4,447,777 | 5/1984 | Sharp et al. | 324/220 |
| 4,463,313 | 7/1984 | Steingroever et al. | 324/243 |
| 4,495,466 | 1/1985 | Lakin | 324/242 |
| 4,528,856 | 7/1985 | Junker et al. | 73/779 |
| 4,534,405 | 8/1985 | Hulek et al. | 164/451 |
| 4,634,976 | 1/1987 | Tiitto | 324/240 |
| 4,881,030 | 11/1989 | Stuecker et al. | 324/209 |
| 5,008,621 | 4/1991 | Jiles | 324/227 |
| 5,010,299 | 4/1991 | Nishizawa et al. | 324/209 |
| 5,012,189 | 4/1991 | Jiles | 324/209 |
| 5,059,903 | 10/1991 | Otaka et al. | 324/223 |
| 5,134,367 | 7/1992 | Griffith et al. | 324/220 |
| 5,204,622 | 4/1993 | McCaslin et al. | 324/220 |

OTHER PUBLICATIONS

"Effects of Grain Size, Hardness, and Stress on the Magnetic Hysteresis Loops of Ferromagnetic Steels," by Kwun et al., J. Appl. Phys. 61(4), 15 Feb. 1987, pp. 1576–1579.

Primary Examiner—Sandra L. O'Shea
Assistant Examiner—Jay M. Patidar
Attorney, Agent, or Firm—Leydig, Voit & Mayer, Ltd.

[57] ABSTRACT

A magnetic inspection head adapted for use with samples having non-planar surfaces. A magnetically permeable core has a pair of poles joined by a magnetically permeable bridge to form a closed magnetic circuit between the pole legs, bridge and the test material. Each pole has magnetically permeable support means terminating in a magnetically permeable deformable surface for engaging the sample. The support means is yieldable such that when the inspection head is placed in contact with the irregular surface of the sample, the deformable surface is deformed to accommodate the shape of the sample with minimal air gaps therebetween. Preferably, the deformable surface is provided by a plurality of pins slidably engaged in a pole structure and urged outwardly for contact with and conformance with a non-planar sample surface.

16 Claims, 6 Drawing Sheets

MAGNETIC INSPECTION HEAD SUITED FOR CONTOURED OR IRREGULAR SURFACES

FIELD OF THE INVENTION

This invention relates to non-destructive evaluation of materials, and more particularly to an improved sensing head for making magnetic measurements.

BACKGROUND OF THE INVENTION

It is often desirable to evaluate the properties of a material without damaging the specimen being tested. Several known techniques make use of magnetic measurements to evaluate specific properties in a specimen sample. Advances in those techniques provide the ability to obtain meaningful information regarding less pronounced intrinsic properties of a material through measurement of magnetic properties. For example, it is known that coercivity can be used to detect plastic deformation and hardness, that maximum differential permeability can be used to measure stress, that remanence can be used to detect creep damage, that a combination of remanence and coercivity can be used to detect impending fatigue failure, and that hysteresis loss can be used to detect changes in grain boundary segregation arising from temper embrittlement.

This ability to correlate the magnetic characteristics of a material to its less pronounced intrinsic physical properties is disclosed in U.S. Pat. Nos. 5,008,621 and 5,012,189, both of which issued to the present inventor. As is recognized in the art and taught by these patents, bulk magnetic properties such as coercivity, remanence, hysteresis loss, initial permeability, maximum differential permeability and anhysteretic permeability may be derived from magnetic hysteresis curves. As is well known, the magnetic hysteresis curve is a plot of flux density B in a material with respect to a varying applied magnetic field intensity H. Both the '621 patent and the '189 patent further teach that information regarding the physical properties of a sample specimen may be obtained from the evaluation of the magnetic properties occurring therein.

In order to obtain the hysteresis curves important to such studies, a magnetic sensing head is required to magnetically excite the material and measure its response. Typically, magnetic inspection heads have consisted of a substantially "C" shaped core having a pair of legs terminating in a pair of co-planar pole faces, so that when the core is placed on a planar sample, both pole faces are in contact with the surface of the sample. The core is wrapped with a power coil which generates a magnetic field when energized. A sensing coil is also wrapped on the core to detect the magnetic flux Φ in of the material under the action of the applied field. The core is placed on the surface of a sample such that a magnetic circuit is created including the core and the test material. When both the surface of the test material and the pole faces of the inspection head are planar, placement of the sensing head on the surface of the sample creates a magnetic circuit which has only very small air gaps between the pole faces and the sample. If the sample is not planar, larger and often variable air gaps will result, with the variation depending on how the inspection head is placed on the sample. The air gaps will have a substantial effect on the measurements being taken, and thus the system is no longer measuring primarily the characteristics of the material, but also the characteristics of the variable air gap. As a result, the ability to analyze materials which are non-uniform or non-planar has encountered these problems of the variable air gap.

Thus, while magnetic measurement techniques have progressed using automated and computerized systems as disclosed in the above-referenced patents, difficulties have been encountered in taking magnetic measurements of non-planar surfaces. It is well appreciated that a magnetic inspection head is not a point contact device, and must have two areas of preferably uniform contact with the surface of the specimen to be tested. The magnetic field is coupled into the sample via those two areas, and the sample in effect becomes part of the magnetic circuit together with the inspection head. When the surface is non-planar, undulating or contoured, it is difficult if not impossible to get uniform contact between the inspection head and the surface using the standard C core inspection head. The repeatability of the measurements can therefore be very dependent on the technique of the user in applying the inspection head to the surface. For example, if the inspection head has two coplanar poles which are on the order of 1.0 square inches in area separated by a gap of about 1 inch, if the surface to be measured does not provide a planar area capable of accommodating that probe, the probe will then be applied with at least some area of the pole faces having a substantial air gap separating it from the sample. The manner in which the operator applies the inspection head to the sample will determine how much of the pole face is in contact with the surface and how much is separated by an air gap of unknown dimension. The repeatability of such measurements from sample to sample, or the ability to measure a sample and calibrate it to a standard in such an arrangement is very severely limited.

Even the ability to take magnetic measurements on non-planar surfaces of substantially uniform contour, such as large pipes, can be adversely impacted by the use of typical prior art probes. For example, if one limits the measurements to the axial direction of the pipe, and tries to arrange the probe such that the poles are tangential to the surface, the measurements may be repeatable from measurement to measurement. However, whenever the probe is displaced slightly from its intended position, the readings will be impacted, even in this not usual measurement situation.

SUMMARY OF THE INVENTION

In view of the foregoing, it is a general aim of the present invention to provide a magnetic inspection head which accommodates for non-planar surfaces by providing minimum air gap coupling between the head and the non-planar surface.

In accomplishing that aim, it is an object of the invention to provide a magnetic inspection head with conformable pole faces which adapt to the shape of the sample surface when the inspection head is brought into contact with the sample.

Generally an object of the invention is to simply and effectively eliminate the air gap variations which had heretofore been present in making magnetic measurements on non-planar surfaces of samples.

An object of the present invention is to provide a magnetic inspection head having a pair of magnetic poles for contact with the specimen to be measured, each pole being comprised of a plurality of projecting magnetic elements adapted to individually contact the portion of the sample surface with which they are associated.

It is a feature of the invention that the magnetic inspection head can be used to provide repeatable and reliable measurements of magnetic samples having non-planar surfaces. The surfaces can be smoothly undulating or irregularly varying, and the pole pieces of the inspection head are adapted to conform with the sample surface, so that the magnetic field in the core is coupled to the surface with a negligible air gap between the pole pieces and the sample.

According to a preferred implementation of the invention, each pole piece is made up of an apertured magnetic support carrying a plurality of individually slidable pins arranged in arrays, with the arrays of pins being energized to couple a magnetic field into the sample. The ability of the pins to project different distances beyond the pole serves to accommodate irregularities in the surface of the sample.

It is an important advantage of the invention that samples of irregular surface configuration can be measured reliably with the inspection head, with the variations of air gap which had been encountered heretofore using planar inspection heads being eliminated by the ability of the inventive inspection head to provide poles which conform to the surface of the sample.

Other objects and advantages will become apparent from the following detailed description when taken in conjunction with the drawings, in which:

DETAILED DESCRIPTION OF THE PREFERRED EMBODIMENTS

While the invention will be described in connection with certain preferred embodiments, there is no intent to limit it to those embodiments. On the contrary, the intent is to cover all alternatives, modifications and equivalents included within the spirit and scope of the invention as defined by the appended claims.

Figure 1:
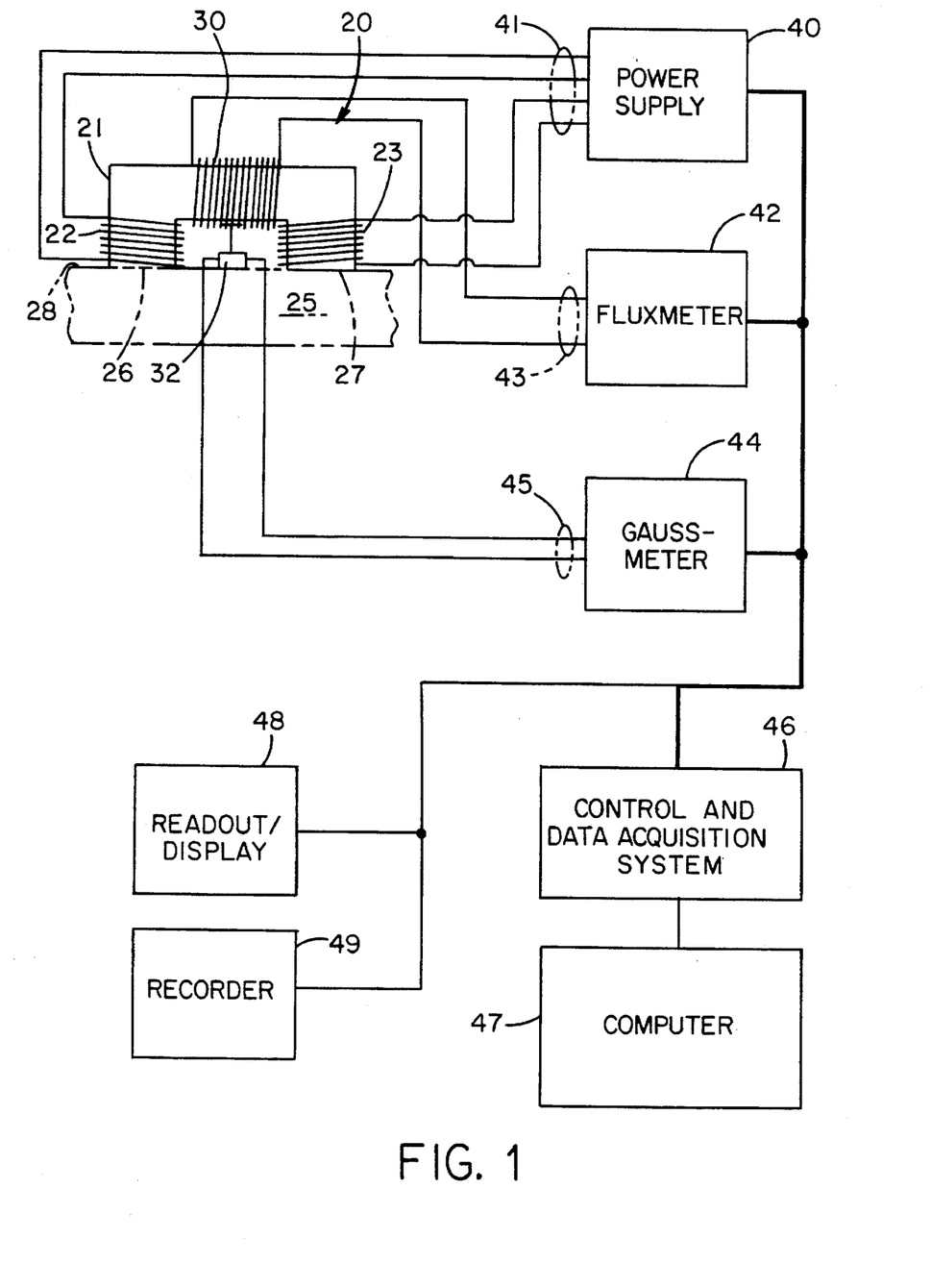
FIG. 1 is a block diagram of a magnetic inspection system illustrating the major electrical and electronic components useful in analyzing magnetic properties of materials.

Turning now to the drawings, FIG. 1 shows a block diagram illustrating the major components of a magnetic inspection system in which the present invention can be employed. An inspection head is generally illustrated at 20 and includes a magnetic core 21 having a pair of power coils 22, 23 wound on the respective legs thereof. Currents in the power coils induce a magnetic field in a magnetic circuit including the core 21 and a test sample 25 (illustrated in dashed lines below the core). The poles have pole faces 26, 27 which are substantially in contact with the upper surface 28 of the sample 25 so that the air gap between the pole faces and the sample is at a minimum. Thus, the magnetic circuit includes the core 21, the sample 25 and the very small air gap separating them. A flux coil 30, also wound on the core 21, measures the flux level created by the magnetic field in the magnetic circuit. Thus, a signal taken from flux coil 30 provides a measure of the response of the sample 25 to the field induced by the power coils 22, 23.

In many cases, the inspection head 20 also includes a surface probe 32, usually a Hall probe, so positioned as to be in contact with the surface 28 of the sample 25. The Hall probe can measure the magnitude of the magnetic field strength produced by the power coils 22, 23 along a line joining the poles 26, 27. Positioning the Hall probe at the surface 28 of the sample 25 provides an indication of the field strength in the sample near the surface, which is also useful information in measuring the magnetic properties of the sample. In particular, the output of flux coil 30 is usually measured as a function of the magnetic field indicated by the output of the Hall probe 32.

The magnetic inspection system includes a bipolar power supply 40, usually computer controlled. The power supply supplies drive currents at respective levels coupled through electrical leads 41 to the power coils 22, 23 to generate magnetic fields of known strength, with the flux coil and Hall probe (when present) adapted to measure the response of the sample to fields of that strength.

For measuring the response of the sample, the flux coil 30 is coupled to a fluxmeter 42 via leads 43. The fluxmeter 42 processes the signal from the flux coil 30 to produce an output signal which is a measure of flux in the sample. Similarly, the Hall probe (or surface probe) 32 is connected via leads 45 to a gaussmeter 44 which processes the signal from the probe to produce a measure of magnetic field strength at the surface of the sample. The elements 40, 42 and 44 are typically controlled by a control and data acquisition system 46 shown connected to its driven elements by a single bus. Typically, the control and data acquisition system 416 is a microprocessor-based unit capable of supplying control signals to the controlled elements (for example, to set the power levels and polarity of the power supply 40), and to further process the signals from the fluxmeter 42 and gaussmeter 44. The control and data acquisition system provides for user interface through a control computer 47 which typically includes a keyboard and a display, such as a CRT. Information about readings to be taken, settings to be made and the like, is provided by a readout/display 48 which is usually the monitor screen of the computer. Certain magnetic inspection systems may also include a recorder 49, which can be an x-y recorder, a tape device, a magnetic memory, or the like, intended to record signals, either raw signals or processed signals, intended to be analyzed for the magnetic or intrinsic properties of the sample being tested.

When using a system such as that illustrated in FIG. 1, the control and data acquisition system 46 controls the power supply 40 to produce bipolar drive currents to the power coils 22, 23, and the fluxmeter 42 and gaussmeter 44 record the response of the samples, The information about the drive and response is processed, displayed and recorded as desired. Hysteresis curves can be produced as well as information for other magnetic studies of the magnetic materials being tested.

As noted above, when attempting to study samples having surfaces of non-planar characteristic, systems such as that shown in FIG. 1 encounter difficulties in obtaining repeatable measurements due to the nonuniform nature of the surface. The measurements can be very dependent on the manner in which the inspection head is placed on the surface, because typically only a small percentage of the area of each pole face will be in actual contact with the sample. Thus, the manner in which the inspection head is placed determines the size, shape and configuration of the air gap between the majority of the pole face and the sample. Since the air gap is much less permeable than the material of the sample or the core, the air gap can provide a much more significant effect on the overall reading than subtle changes in the magnetic character of the sample to be tested. Thus, the information being sought is often lost in the noise created by the fact that the inspection head and sample are, to a certain extent, geometrically incompatible.

In accordance with the invention, an inspection head is provided which has pole faces of conformable character, such that positioning the inspection head on a sample with a non-planar surface causes conformation of the pole faces to maintain substantial contact between the area of each pole face and the sample surface. Thus, the variations in the air gap heretofore caused by undulating sample surfaces are substantially eliminated, and the readings taken are primarily determined by the characteristics of the sample. It is a feature of the invention that the deformable pole faces are implemented with minimum variation in the magnetic circuit of the core so as to avoid introducing an array of new problems resulting from the solution to the air gap problem. Thus, as will be explained in greater detail below, the power coils are preferably wound directly on the extending core legs which support the deformable pole faces, and both the support and the bridge which carries the support are highly permeable materials so that the variations in the length of the support which are necessary to accommodate an undulating surface do not themselves introduce substantial changes in the measurement of the magnetic response.

Figure 2:
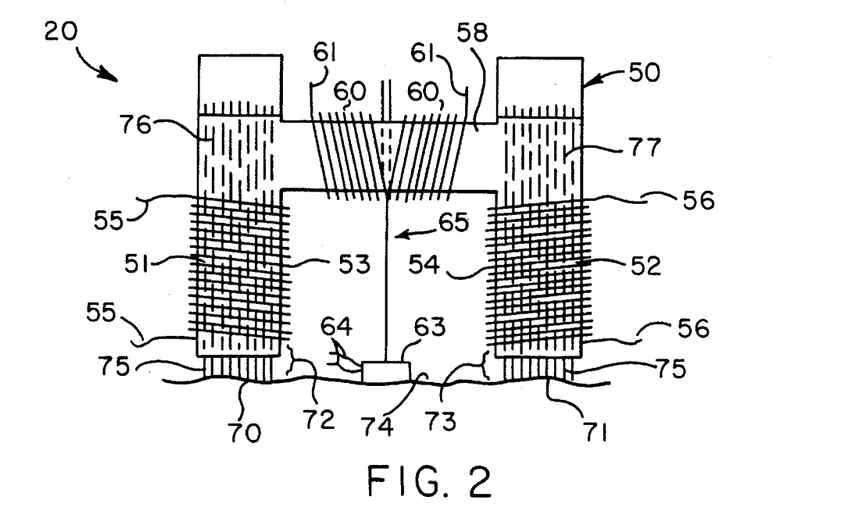
FIG. 2 is a schematic diagram illustrating the principles of an inspection head exemplifying the present invention.

Turning to FIG. 2, there is schematically shown an inspection head 20 in somewhat greater detail than the illustration of FIG. 1. A high permeability magnetic core 50 includes a pair of pole pieces 51, 52. Power coils 53, 54 are wound on the respective pole pieces 51, 52. The coils have leads 55, 56 for connection to the power supply of FIG. 1.

As shown in FIG. 2., the core 50 has a bridge member 58 joining the pole pieces 51, 52. The pole pieces 51, 52 and bridge member 58 are preferably formed of the same material, preferably a high permeability material, such as Armco iron or permalloy. Disposed on the bridge element 58 is a flux coil 60 having leads 61 adapted for connection to the fluxmeter 42 of FIG. 1. The flux coils can also be wound on the respective legs. FIG. 2 also shows a surface probe 63, preferably a Hall probe, having four leads 64 adapted for connection to the gaussmeter 44 of FIG. 1.

In accordance with an important aspect of the invention, each of the pole pieces 51, 52 is provided With a pole face generally illustrated at 70, 71 which is deformable in order to conform to a non-planar or undulating surface 74 of the sample to be measured. The pole pieces 51, 52 are joined to the deformable pole faces 70, 71 by support means generally indicated at 72, 73 which maintains the magnetic integrity of the pole piece while at the same time allowing deformation of the pole faces 70, 71. The support means 72, 73 is illustrated only schematically in FIG. 2. Generally, it can be seen that the distal end of each pole (the end distant from the bridge 58) is formed of a plurality of magnetically permeable pins 75 engaged in mating apertures in the structure of the pole face 51, 52. The pins are supported for translation into or out of the respective apertures, and are biased outwardly as suggested by dashed lines 76, 77. Thus, when the inspection head is placed against a surface 74 to be inspected (with the pole faces against the surface), the pole faces are allowed to deform by accommodation of the support elements 72, 73. The system thereby provides a continuous high permeability magnetic circuit through the core (including pins and support members), through the minimum or negligible air gap between the deformable pole faces 70, 71 and the undulating or variable surface 74 of the sample, and through the sample itself. Thus, when the power coils 53, 54 are energized to induce a magnetic field in the magnetic circuit, that field is closely coupled at the pole faces 70, 71 into the sample, and the flux coil 60, as well as the surface probe 63, can measure the response of the sample to a tightly coupled magnetic field, in which coupling is not dependent on a variable air gap between the pole faces and the sample.

A support or loading means 65 is associated with the surface probe 63 and functions to bias the surface probe 63 against the surface 74 of the sample, between the pole faces 70, 71. With the surface probe, such as a Hall probe, thus positioned, the Hall probe will measure the tangential component of the magnetic field running perpendicularly to a line joining the centers of the pole faces 70, 71. The adjustable mounting arrangement 65, illustrated only schematically in FIG. 2, can consist of any non-magnetically permeable support member capable of so-positioning the surface probe. Thus, a spring-like brass mounting strip shaped in zig-zag or fan fold arrangement can be affixed to the central bridge member of the core to press the surface probe outwardly away from the core. Alternatively, a pin, similar to the pins of the pole arrays, but constructed of material which is not substantially permeable, such as aluminum, can be forced downwardly, like the pins of the pole faces, to force the Hall probe into contact with the surface of the sample.

Figure 3:
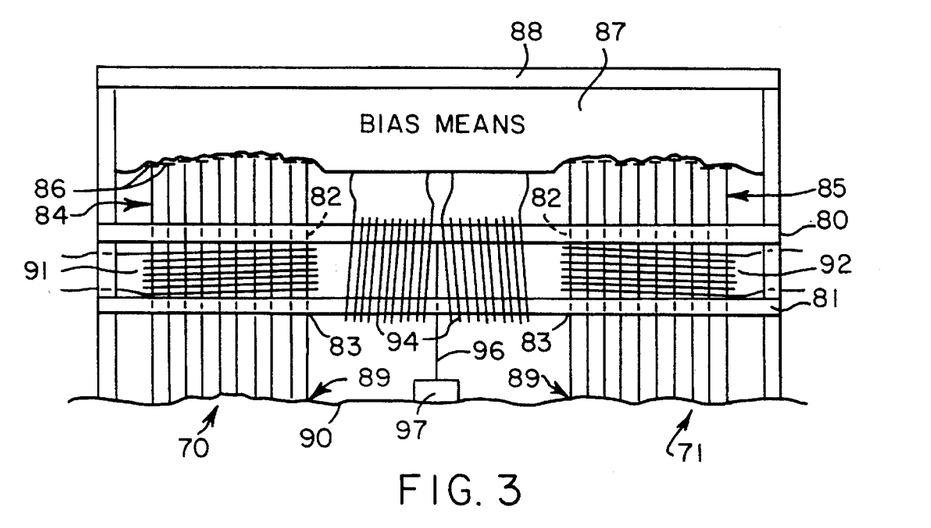
FIG. 3 is a diagram in front elevation illustrating an inspection head exemplifying the present invention.

Turning to FIG. 3, there is illustrated, also in somewhat diagrammatic form, another form of magnetic inspection head in accordance with the invention. In the FIG. 3 illustration, the bridge member comprises a pair of flat rectangular plates 80, 81 providing respective arrays of apertures 82, 83 which carry arrays of pins 84, 85 which in turn define the respective pole faces 70, 71. The upper plate 80 is of high permeability magnetic material, such as Armco iron or permalloy, and provides the flux return path for the magnetic circuit which includes the power coils, the core and the test sample. The lower plate 81 is included primarily to stabilize the elongated pins, and should not provide a flux path between the coils, because it would be a leakage path in shunt with the sample. Thus, the lower plate 81, when it is used, is of low permeability material, such as plexiglass or aluminum.

Arrays of apertures 82 and 83 in the plates 80, 81 are provided to allow arrays of pins 84, 85 to be positioned within the apertures for sliding engagement therein. The pins are illustrated as having blunted heads 86 at the proximal ends thereof. The heads, in turn, are associated with pin loading means 87 disposed between a fixed plate 88 in the inspection head and the heads 86 of the pins. The pin loading means 87 can take various forms as will be described in greater detail below, but the function is to provide a force urging the pins 84, 85 outwardly so that the distal ends 89 of the pins will contact the non-planar surface 90 of the sample to be tested. A pair of power coils 91, 92 are wound to encircle the pins of each pole, and are disposed between the bridge member (plate 80) and the sample. Accordingly, the field which is created by energization of the coils 91, 92 will create flux paths which traverse the pins 84, 85, the negligible air gap between the distal ends 89 of the pins and the surface 90 of the sample, the sample, and the magnetically permeable portion 80 of the bridge member. A flux coil (or pair of flux coils), designated generally at 94, is wound on the central portion of the bridge, or preferably around one of the legs of the poles 70 or 71, so that changes in the magnetic flux in the coupled system (which includes the sample) will be sensed by the flux coil so as to provide a measure of the magnetic flux passing through the test sample. A surface probe 97, preferably a Hall probe, is mounted between the poles 70, 71, on a line joining the poles, and is mounted by support means 96 to force the Hall probe 97 into contact with the surface 90 of the sample. The Hall probe thereby measures the tangential field between the pole faces 70, 71 at the surface of the sample.

In FIG. 3, the pin loading means 87 associated with the arrays 84, 85 of pins, is illustrated schematically, to account for the fact that such means can take various forms. However, whether simple or complex, the function of the pin loading means 87 is simply to urge the pins 84, 85 outwardly of the inspection head so that the distal ends 89 serve to contact a non-planar surface 90 when the inspection head is disposed on the sample. The pins 89 are constructed of high permeability magnetic material, such as Armco iron, and are intended to be of sufficient diameter to be self-supporting and to provide an adequate fill factor such that the conformable pole face defined at the distal ends 89 has a substantial proportion (such as 50%) of the total area defined by the pole occupied by highly permeable magnetic material. It will be appreciated that the rest of the area is, of course, occupied by the air which is between the pins, but this is not an "air gap" as such because it is not part of the circuit. It is also preferable to relate the cross-sectional area of the bridge member, i.e., the cross section of the permeable plate 80 to the area of the pins in a pole face, particularly when using the same material for the bridge member and the pins, so that the cross section of the magnetically permeable material in the inspection head remains substantially constant throughout the inspection head, and the inspection head itself introduces no substantial discontinuities in the magnetic circuit. In that respect, it is also preferable to provide relatively closely fitting apertures 82 in the high permeability plate 80 so as to minimize the air gap between the pins and the bridge member, and enhance the continuity of the flux path from the bridge to the pole elements of the inspection head. The apertures 83 of the non-magnetically permeable plate 81, which serve primarily a guiding function, can be made somewhat larger if desired so that the pin loading means 87 need not apply excessive force in order to assure that all of the pins of each pole face are urged into contact with the non-planar surface of the sample.

Magnetic inspection heads according to the invention can be configured for various applications, such as relatively simple applications where the parts are only slightly contoured, and very little demand is placed on the pin loading system, to substantially complex situations where the surface of the sample to be tested can be highly irregular. It is within the skill of the art, based on the teachings of this application, to configure an inspection head with the appropriate characteristics needed to provide adequate pin loading force to meet the type of application for which the probe is intended.

In one particular implementation of the invention, each of the pole faces 70, 71 can be configured by means of a square array of pins measuring approximately 1" on each side, with the center-to-center spacing between the pole faces being approximately 2.5". It will thus be appreciated that a sample surface area of about 3½"×1" must be provided for accommodating the inspection head, and the suitability of an inspection head according to the invention to accommodate irregularities or non-planarities in that surface will now be apparent.

Figure 4:
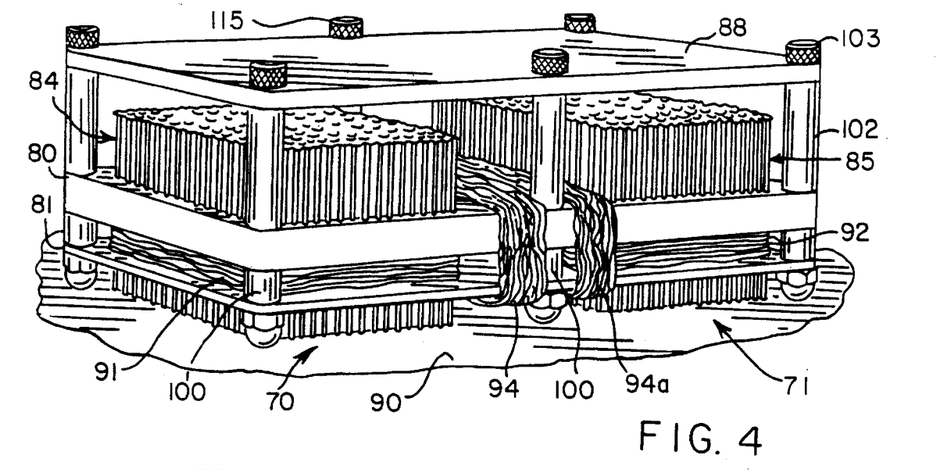
FIG. 4 is a perspective view of one form of an inspection head according to the invention.

FIG. 4 illustrates in greater detail the structural configuration of an inspection head of the type illustrated schematically in FIG. 3. It will be seen that a high permeability rectangular plate 80 and a low permeability guide plate 81 are separated by a series of spacers 100. A low permeability upper plate 88 is also separated from the high permeability plate 80 by another array of spacers 102, with a plurality of bolts 103 joining the spacers 100, 102 and the plates 80, 81, 88 to provide a unitary relatively rigid support structure.

As noted in connection with FIG. 3, the upper plate 80 (the plate disposed above the power coils) is of high permeability material, and has a cross-sectional area approximately equivalent to the total cross-sectional areas of all the pins in one of the arrays. The guide plate 81 and the top plate 88 are of non-permeable material, such as plexiglas or aluminum. The mounting devices such as the spacers 100, 102 and the bolts 103 are also of non-permeable material, such as brass or aluminum. The Hall probe 97 is not visible in the diagram of FIG. 4, but it is seen in FIG. 6 (a plan view of the inspection head of FIG. 4) to be centrally located, on a line joining the centers of the pole arrays 70, 71.

Power coils 91, 92 are wrapped around the arrays 84, 85 of pins which form the pole faces 70, 71. In a simple embodiment, the coils 91, 92 are wound loosely around the outer pins in the respective arrays. Alternatively, a thin, non-permeable coil form 106, such as illustrated in plan view in FIG. 6 and in cross section in FIG. 7 is employed. The coil form is preferably of thin material such as a cardboard or plastic formed into an appropriate rectangle and fixed, such as by gluing, to the core plate 80. The coil forms 106 serve to provide general support for the coils 91, 92 when wound on the forms so as to facilitate the translation of the pins at the outer periphery of the array.

The sensing coils 94, as illustrated in FIGS. 4–7, are shown wound centrally on the arrays 70, 71, but can also be wound on the coil forms 106, which location is preferably due to flux leakage. When central supporting bolts and spacers 115 are utilized, a pair of sensing coils 94, 94a can be disposed on either side of the central support 115. The coils are wound about the upper support plate 80 (the magnetically permeable plate) and the lower guide plate 81, as best shown in FIG. 4. When tighter coupling is desired, the sensing coil can be wound only about the magnetically permeable plate 80 before the lower guide plate is put in place. Thus, the sensing coils can be wound at the same stage of assembly as the power coils 91, 92, and before the guide plate 81 is brought into position. Alternatively, they may be wound on the coil form 106 before the power coil is wound on the form. In either case, the sensing coils 94 are coupled to a magnetically permeable portion of the bridge member so that any changes in the magnetic circuit (and the changes include primarily changes in the magnetic structure of the sample) are sensed by the coil 94.

Figure 6:
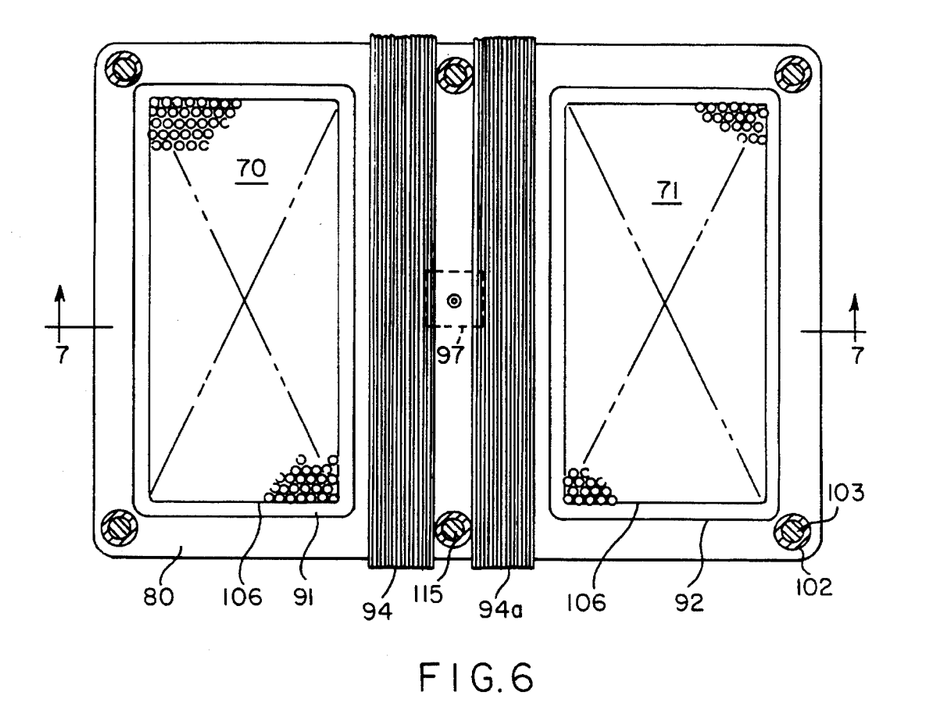
FIG. 6 is a plan view of the inspection head of FIG. 4 with the top plate removed.
Figure 7:
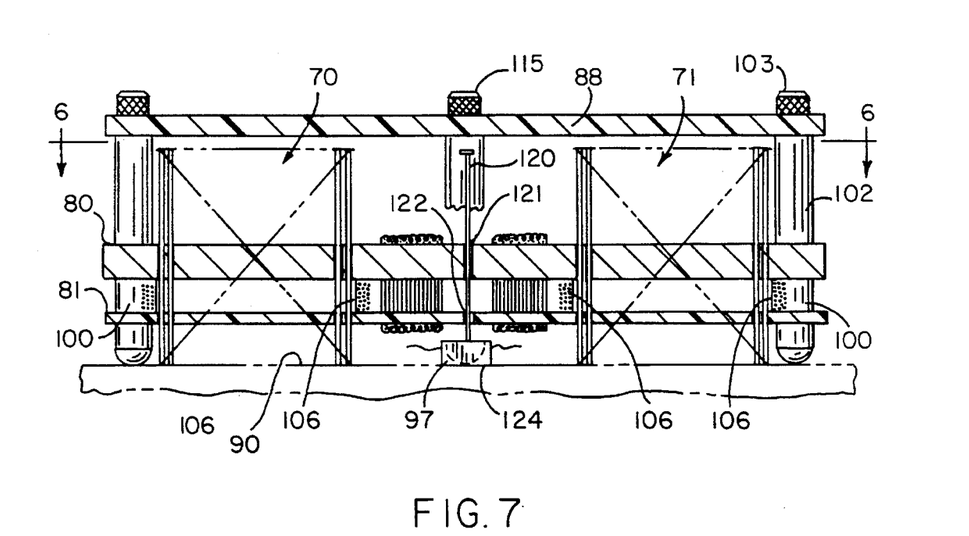
FIG. 7 is a sectional view taken along the line 7—7 of FIG. 6, showing the surface sensor and its attachment to the inspection head.

As best shown in the diagrams of FIGS. 6 and 7, the inspection head includes a surface probe, shown herein as a Hall probe 97. The Hall probe 97 is located centrally in the bridge member on a center line between the poles. As best shown in FIG. 7, the Hall probe 97 is supported on a pin 120 (which should be a low permeability material, unlike the pins 84 and 85) disposed in apertures 121, 122 in the plates 80, 81, respectively. Like the pins of the poles, the pin 120 is loaded downwardly by its own weight (and the weight of the Hall probe) such that the lower surface 124 of the Hall probe 97 will contact the upper surface 90 of the sample to measure the field strength in the sample at the tangent of the surface on a line joining the center of the poles 70, 71.

The diagram of FIG. 6 also illustrates the substantial fill factor achieved by the pins 84, 85 which make up the pole faces. FIG. 6 is a plan view, and thus the upper portion of the illustrated pins are actually the heads of the pins. However, the pins are constructed such that the diameter of the shank portion is also relatively thick (as compared to the head). The pins are also preferably un-tapered to render uniform the magnetic field carried through the poles irrespective of whether the pins are substantially confined within the inspection head or extend a substantial distance therefrom. It will be seen in FIG. 6 that the pins from row to row are preferably offset to enhance the fill factor and render as much as possible of the areas of the poles 70, 71 to be composed of magnetically permeable material, as contrasted with the non-permeable air which separates the magnetically permeable pins.

The illustration of FIG. 4 utilizes only the weight of the pins in the array as the pin loading means for assuring contact between the distal ends of the pins and the sample surface. This is the least complex configuration of an inspection head according to the invention, but requires that the inspection head be used primarily in a horizontal orientation. In some cases, the use of such a head requires care, such as tapping of the inspection head and the like to assure that the pins drop down through the apertures in the guide plate to contact the sample, before the inspection system (FIG. 1) is energized to take a series of readings.

Figure 5:
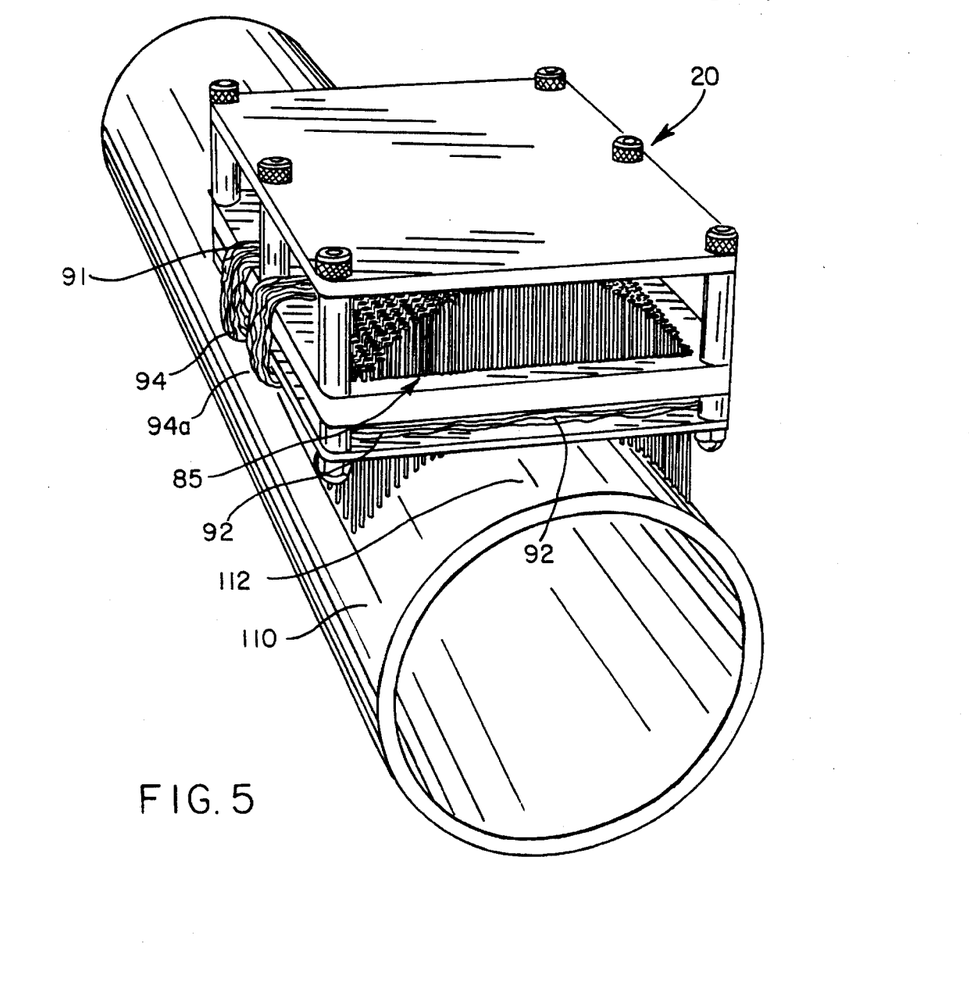
FIG. 5 is a view of the inspection head of FIG. 4 in contact with a sample to be tested.

The orientation of such an inspection head on a smoothly contoured pipe is illustrated in FIG. 5. FIG. 5 thus shows a magnetic inspection head 20 of the type generally illustrated in FIG. 4 disposed on a sample 110 in the form of a common cylindrical pipe of reasonably substantial diameter. The inspection head 20 is used in a horizontal attitude, and when the inspection head is placed on the surface 112 of the sample 110, care is taken to assure that all of the pins in respective arrays 84, 85 drop into contact with the surface 112 of the pipe. In that configuration, the power coils 91, 92 are energized and signals through the sensing coil 94A detected to determine the magnetic characteristics of the material. At the same time, the Hall probe (not seen in FIG. 5) is also electrically monitored to determine a measure of field strength at the surface of the sample between the pole faces. Thus, by detecting flux in the sensing coil 94 as well as field strength in the Hall probe 97, the system can cycle the power coils 91, 92 through a series of current levels and polarities, to obtain a relatively complete signature of the magnetic characteristics of the sample in the area occupied by the inspection head. Moving the inspection head along the pipe, or disposing it on a pipe of the same cross-sectional shape, should generate identical readings for samples of identical magnetic characteristics, because the inspection head assures minimum air gap between the distal ends 89 of the pins and the sample surface 112, so that any changes in either the field strength or flux linkage sensed by the sensing coil or Hall probe will be known to result from changes in the magnetic properties of the sample, rather than changes in the manner in which the inspection head is applied to the sample.

FIG. 5 also illustrates the effectiveness of the use of gravity as the pin loading means in limited applications of an inspection head according to the invention. Thus, the pins in the apparatus of FIG. 5 are of magnetically permeable material, such as Armco iron, which not only has the useful property of high magnetic permeability, but also of relatively high density. The apertures 82 in the magnetically permeable plate 80 are rather closely fitting, but allow a sliding fit of the pins in the apertures. The apertures 83 in the lower guide plate 81 can be somewhat larger so as to prevent binding of the pins, allowing free sliding of the pins downwardly to contact the surface. When the inspection head 20 is removed from the sample, all of the pins will project substantially all the way out of the inspection head, and when the inspection head is again positioned on a sample, the pole faces will conform to the sample by being deflected upwardly against the force of gravity into the inspection head. When care is used with such an inspection head, no additional pin loading force will be required.

Figure 8:
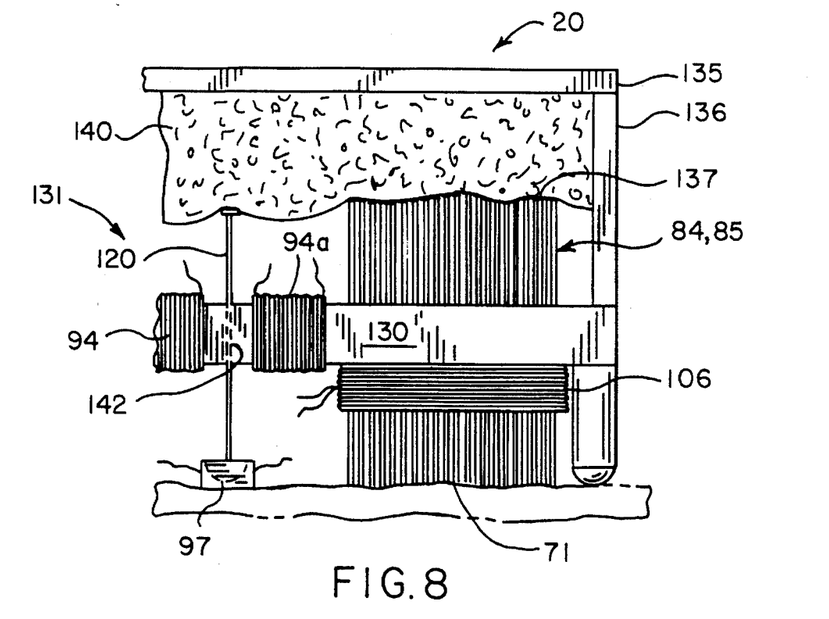
FIG. 8 is a partial front elevation of an inspection head showing a presently preferred form of loading means for urging the pins of the pole outwardly.
Figures 9, 10:
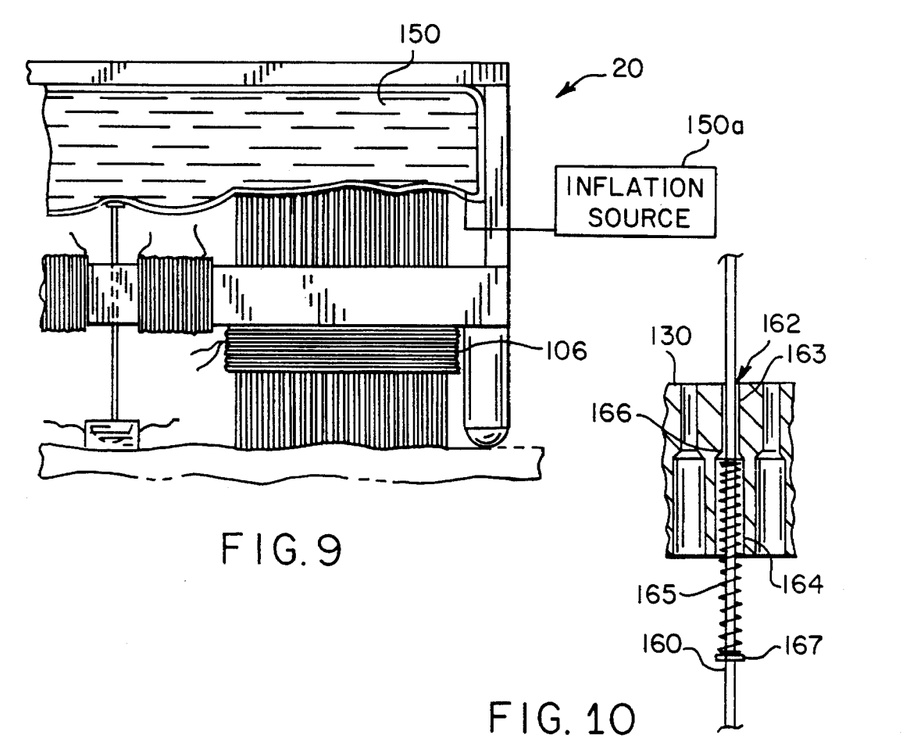
FIG. 9 is a view like FIG. 8 but illustrating an alternative loading means.
FIG. 10 is a diagram illustrating a single pin carrying its own pin loading means.

FIGS. 8–10 illustrate embodiments of the invention utilizing alternative forms of pin loading means. Turning to FIG. 8, there is shown the currently preferred embodiment of pin loading means used in the practice of the invention. The sensing head 20 of FIG. 8 is a slight variation on that illustrated in connection with FIGS. 4, et seq., in that only a single magnetically permeable plate is utilized to support the pins, in contrast to a pair of plates 80, 81 in the previous embodiment. Thus, a relatively thick magnetically permeable plate 130 is provided, having apertures therethrough into which the pins 84, 85 forming the poles are adapted to project. The plate 130 is of high permeability magnetic material, such as Armco iron or permalloy, and the apertures are configured with respect to the cross section of the pins for a sliding fit to provide tight magnetic coupling to the pins while allowing the pins to slide within the apertures. Use of a relatively thick plate 130 (which can be on the order of ½ inch thick) dispenses with the need for a second guide plate. In order to render the cross section of the bridge member more or less equivalent in area to the composite cross section of the pins occupying each pole, the central portion 131 of the bridge can be appropriately shaped or thinned to achieve the desired cross-sectional area. It will also be seen that the central coil 94 is wound directly on the plate 130 so that it contacts all four faces thereof for tighter coupling of the sensing coil to the magnetic structure than is achieved in the embodiment of FIG. 4.

As in the FIG. 4 embodiment, the sensing head 20 of FIG. 8 includes an upper plate 135 which is fixed as by spacers and bolts generally indicated at 136 to the lower plate 130. In practicing the invention, disposed between the upper plate 135 and the proximal ends 137 of the pins 84, 85 is a pin loading means, shown herein as an elastomeric cushion 140. The cushion 140 is of sufficient resiliency to urge the pins outwardly to achieve all necessary configurations of the conformable shape of the pole 71 which is to be accommodated by the magnetic inspection head. Thus, with samples of slight surface irregularities such as that illustrated in FIG. 8, the cushion 140 can be of foam rubber, neoprene or the like, and will urge all pins outwardly even in the presence of nonsevere undulation in the surface of the sample. In cases where the surface undulations are intended to be more extreme, the support members 136 are configured to allow for a thicker cushion 140, such that pin-to-pin deviations required by more irregular surfaces can be accommodated without substantial percentage increase in thickness of the pad 140.

The embodiment of FIG. 8 also illustrates the Hall probe 97 mounted on an aluminum or brass pin 120 fit through an aperture 142 in the plate 130, and urged downwardly by the same elastomeric cushion 140 which acts on the pole pins. Thus, the Hall probe 97 is also urged into contact with the surface of the sample to achieve accurate measurements.

FIG. 9 is like the embodiment of FIG. 8, except that the elastomeric cushion 140 is replaced by a fluid (i.e., liquid or gas) filled bladder 150. An auxiliary apparatus 150a is provided with the embodiment of FIG. 9, and is adapted to inflate the bladder 150 (with liquid or gas) after the inspection head is disposed on the surface. The embodiment of FIG. 9, while somewhat more complex to use because of the necessity to fill or empty the bladder 150 provides for greater assurance of conformability of the conformable pole faces to the undulating or non-planar surface of the sample.

FIG. 10 illustrates another alternative embodiment of the invention in which each of the pins carries its own pin loading means. It will be seen from FIG. 10 that each pin, represented by pin 160, is disposed in the magnetically permeable core member such as plate 130. A complex aperture 162 is formed in the plate 130 with a first portion thereof 163 closely fitting the shank of the pin 160 to achieve tight magnetic coupling therewith, and a second portion 164 sufficiently large to accommodate a spring 165. The spring 165 is disposed between a shoulder 166 in the complex aperture 162 and a stop member 167 on the pin 160 so as to urge the pin outwardly from the support plate 130. An identical spring-loaded arrangement is provided for each of the pins in the arrays 84, 85, as well as for the central pin 121 supporting the Hall probe. In this fashion, a highly adaptable inspection head is provided with each pin carrying its own pin loading means which is substantially independent of the loading means of adjacent pins, so that very substantial changes in the contour of samples to be tested can be accommodated.

Figure 11:
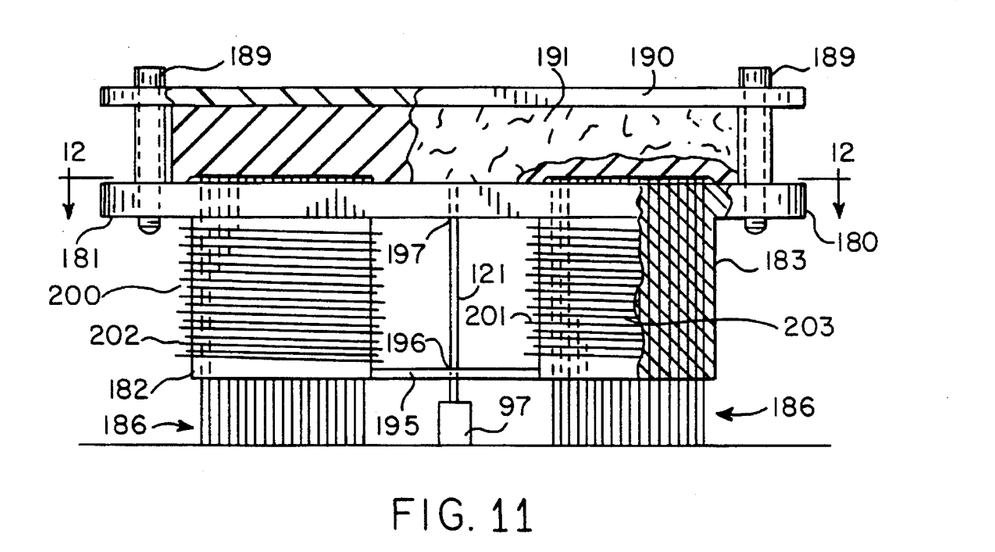
FIG. 11 is a front elevation, partly broken away, showing a presently preferred embodiment of the invention.
Figure 12:
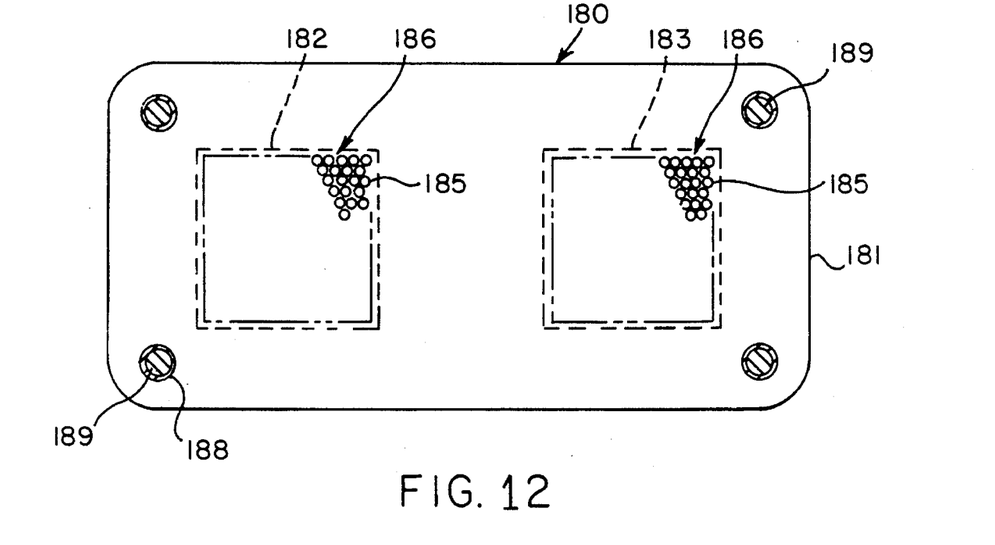
FIG. 12 is a plan view of the magnetic core which serves as the basis for the embodiment of FIG. 11.

Turning now to FIGS. 11 and 12, there is shown yet another embodiment of the invention, currently considered to be the preferred embodiment. Among the advantages possessed by the embodiment of FIGS. 11 and 12 over other embodiments of the invention is a somewhat reduced size, and tighter magnetic coupling to the pins which form the conformable pole faces.

The figures illustrate that this embodiment is based on a core member 180 comprising a unitary magnetic structure having a generally planar or plate-like base 181 and a pair of depending pole pieces 182, 183. The entire core member 180 is formed of a single piece of high permeability metal such as Armco iron. When made in small quantities, the unit can be machined from a block of such material. When made in larger quantities, the legs and planar upper member can be formed by casting following which machining operations can complete the core unit. As best shown in FIG. 12, the depending legs 182, 183 are generally square in cross section. In a preferred embodiment, they are approximately 1"×1" square, and are separated by a gap of only 1", achieving a somewhat smaller shape than the inspection heads described thus far. Formed in each of the leg members 182, 183 are a plurality of apertures 185 adapted to receive pins 186 (FIG. 11) for a sliding fit such as described in connection with the other embodiments. The apertures 185 can be formed by drilling. The base member 181 has only four mounting apertures 188 formed therein for receiving retainers 189 (such as brass screws or the like) adapted to join a top non-permeable plate 190 thereto. The plate 190 serves to compress the pin loading means 191, illustrated as the preferred elastomeric cushion. The pins 186 have flattened heads as described in connection with the other embodiments, such that the elastomeric cushion 191 biases the pins outwardly of the legs 182, 183 to provide deformable pole faces at the distal ends of arrays of pins 186.

As in the other embodiments, a central non-permeable pin 121 carries a Hall probe 97 adapted to contact the surface of a sample. In the FIG. 11 and 12 embodiment, a non-permeable guide plate 195, such as a plexiglass plate, is attached, as by gluing, to the insides of the respective legs 182, 183, and has a central aperture 196 formed therein for receiving the pin 121. The pin-loading means 191 also forces the Hall probe 97 into contact with the sample. In certain embodiments, it is preferable to provide additional guide means for the Hall probe 97 in order to assure its travel directly into and out of the assembly. A certain degree of guidance is provided by the depth of the aperture 197 formed in the flat base member 181 of the core 180. Additional guidance can be provided by depending plexiglass plates (not illustrated in FIG. 11), but which are adapted to depend downwardly from the plate 195 and to partly surround the Hall probe 97, to serve not only a guidance function.

The depending magnetically permeable legs 182, 183, not only provide long guides for the pins 186, but also serve as coil forms for holding the magnetic coils of the inspection probe. Thus, power coils 200, 201 are wound on the respective legs 182, 183. In the present embodiment, flux coils 202, 203 are also wound on the depending legs 182, 183. Both sets of coils, both those which induce the field and those which measure the degree of coupling, are thus wound on magnetic elements of the core which are tightly coupled to the pins, the pins being encased within the entire length of the core on which the coils are wound. Thus, the pins are in the present embodiment surrounded by high permeability magnetic material for the bulk of their length, and the length of the pins which is surrounded by power coils 200, 201 or flux coils 202, 203 is also encased within the high permeability core member. Tighter magnetic coupling is thus achieved by the embodiment of FIGS. 11 and 12.

It will be appreciated that what has been provided is an inspection head which is capable of achieving magnetic measurements much more reliable than those obtained heretofore when studying samples of having non-planar surfaces. In contrast to the solid pole faces of the prior art, the inspection head of the present invention provides a segmented pole face, preferably made up of a plurality of individual pins, to produce a pole face which is conformable, and which when the inspection head is disposed on a sample, conforms itself to the shape of the sample. Pin loading means are associated with the pins to cause conformance of the pole face with the surface of the sample, minimizing air gaps between the pole face and the sample. As a result, the magnetic circuit which includes the poles, the pins, the sample, and the negligible air gaps between the distal ends of the pins and the sample surface will allow measurement of the magnetic characteristics of the material, with the material itself serving as the primary variable from measurement to measurement. As a result, measurements can be obtained which are much less prone to error than those achieved heretofore.

What is claimed is:

1. A magnetic inspection head for measuring magnetic properties of a sample having a non-planar surface, the magnetic inspection head comprising, in combination:

a magnetically permeable core having two arrays of apertures covering substantially similar areas joined by a bridge;

a plurality of magnetically permeable pins in the apertures mounted with their distal ends projecting through the core to form a contact surface, the pins being slidable in the apertures so that they can project by differing amounts through the core;

pin loading means for urging the distal ends of the pins outwardly from the core so that the distal ends of the pins substantially conform to the non-planar surface of the sample with minimal air gaps when the inspection head is disposed on the sample;

power coils associated with the arrays of pins to induce a magnetic field in a magnetic circuit including the arrays of pins, the bridge, and the sample;

a power supply for producing drive currents at controllable levels in the power coils for producing magnetic fields of respectively controllable levels; and flux coil means in the magnetic circuit adapted to measure the response of the sample to the field induced by the power coils.

2. The inspection head as set forth in claim 1 further including a surface sensor located approximately centrally of the inspection head between the arrays of pins, the surface sensor including loading means attached to the inspection head for urging the surface sensor into contact with the surface of the sample when the distal ends of the pins are also in engagement with said surface.

3. The inspection head as set forth in claim 1 wherein the inspection head is adapted for use on horizontally disposed surfaces, and the pin loading means comprises the weight of the pins acting through a loose sliding fit between the pins and the apertures structured to cause the weight of the pins to overcome friction with the apertures so as to employ gravity to urge the pins into engagement with the non-planar surface of the sample.

4. The inspection head as set forth in claim 1 wherein the pin loading means comprises an elastomeric cushion interposed between the proximal ends of the pins and a fixed surface in the inspection head, the elastomeric cushion being sufficiently resilient to urge the pins into contact with the non-planar surface of the sample.

5. The inspection head as set forth in claim 1 wherein the pin loading means comprises a fluid-filled bladder interposed between the proximal ends of the pins in the arrays and a fixed surface in the inspection head, and means for inflating the bladder to impose forces on the proximal ends of the pins adapted to translate the pins through the apertures to urge the distal ends into contact with the non-planar surface of the sample.

6. The inspection head as set forth in claim 1 wherein the pin loading means comprises spring means associated with the respective pins adapted to urge the pins outwardly from the core to accommodate the non-planar surface of the sample.

7. The inspection head as set forth in claim 1 in which the magnetically permeable core includes a generally planar base member and a pair of depending legs of magnetically permeable material, the apertures being formed through the legs and penetrating through the base, the power coils and flux coil means being wound on the respective legs so as to be in magnetic coupling engagement with the legs and with pins disposed in apertures in the legs, the pin-loading means being an elastomeric cushion interposed between the proximal ends of the pins and a fixed surface in the inspection head, the elastomeric cushion being sufficiently resilient to urge the pins into contact with the non-planar surface of the sample.

8. A magnetic inspection head for measuring magnetic properties of a sample having a non-planar surface, the magnetic inspection head comprising, in combination:

a magnetically permeable core having two poles joined by a bridge, each pole having magnetically permeable support means terminating in a magnetically permeable deformable surface for engaging the sample, the support means being yieldable such that when the inspection head is placed in contact with the non-planar surface of a sample, the deformable surfaces deform to accommodate the shape of the sample surface with minimal air gaps therebetween;

power coil means on the core for inducing a magnetic field in a magnetic circuit which includes the core and sample;

a power supply for producing drive currents at controllable levels in the power coils for producing magnetic fields of respectively controllable levels; and flux coil means on the core for measuring the magnetic flux passing through the circuit as the response of the sample to the field induced by the power coil means.

9. The combination as set forth in claim 8 wherein the magnetically permeable core includes legs extending downwardly from the bridge, the power coil means comprises a pair of coils wound on the respective legs, and the magnetically permeable support means magnetically couples the legs to the deformable surface while maintaining the magnetic integrity of the respective poles.

10. The combination as set forth in claim 8 wherein the magnetically permeable core comprises a support member having apertures for slidably receiving a plurality of pins having distal ends adapted to provide said deformable surface, power coils wrapped on the cores in magnetic coupling relationship with the pins so as to maintain the magnetic integrity of the respective poles.

11. The combination as set forth in claim 10 wherein the inspection head is adapted for use on horizontally disposed surfaces, and the support means comprises the weight of the pins acting through a loose sliding fit between the pins and the apertures in the support member structured to cause the weight of the pins to overcome friction with the apertures so as to employ gravity to engage the distal ends of the pins with the non-planar surface of the sample.

12. The combination as set forth in claim 10 wherein the support means includes an elastomeric cushion interposed between the proximal ends of the pins and a fixed surface in the inspection head, the elastomeric cushion being sufficiently resilient to urge the pins into contact with the non-planar surface of the sample.

13. The combination as set forth in claim 10 wherein the support means further includes a fluid-filled bladder interposed between proximal ends of the pins and a fixed surface in the inspection head, and means for inflating the bladder to impose forces on the proximal ends of the pins adapted to translate the pins through the apertures to bring the distal ends into contact with the non-planar surface of the sample.

14. The combination as set forth in claim 10 wherein the support means further includes spring means associated with each said pin adapted to urge the pins outwardly from the core to accommodate the non-planar surface of the sample.

15. The combination as set forth in claim 8 further including a surface sensor for measuring field strength located approximately centrally of the inspection head between the respective poles, the surface sensor including loading means attached to the inspection head for urging the surface sensor into contact with the surface of the sample to measure field strength at said surface when the deformable surfaces are also in contact with said surface.

16. The combination as set forth in claim 8 wherein the magnetically permeable core comprises a generally planar base member and a pair of legs which depend from and are integrally joined to the base member, the legs forming the poles, and including a plurality of apertures for slidably receiving a plurality of pins having distal ends adapted to provide said deformable surface, the power coil means and flux coil means being wrapped on the legs for magnetic coupling with the pins, and an elastomeric cushion interposed between the proximal ends of the pins and a fixed surface in the inspection head, the elastomeric cushion being sufficiently resilient to urge the pins into contact with the non-planar surface of the sample.

* * * * *